US012799074B2

(12) United States Patent
Batra et al.

(10) Patent No.: US 12,799,074 B2
(45) **Date of Patent: *Nov. 17, 2026**

(54) PROCESS TO PREPARE TREPROSTINIL, THE ACTIVE INGREDIENT IN REMODULIN®

(71) Applicant: United Therapeutics Corporation, Silver Spring, MD (US)

(72) Inventors: Hitesh Batra, Herndon, VA (US); Sudersan M. Tuladhar, Silver Spring, MD (US); Raju Penmasta, Herndon, VA (US); David A. Walsh, Palmyra, VA (US)

(73) Assignee: United Therapeutics Corporation, Silver Spring, MD (US)

(*) Notice: Subject to any disclaimer, the term of this patent is extended or adjusted under 35 U.S.C. 154(b) by 544 days.

This patent is subject to a terminal disclaimer.

(21) Appl. No.: 18/215,482

(22) Filed: Jun. 28, 2023

(65) Prior Publication Data

US 2023/0338313 A1 Oct. 26, 2023

Related U.S. Application Data

(60) Continuation of application No. 16/594,737, filed on Oct. 7, 2019, now Pat. No. 11,723,887, which is a continuation of application No. 15/423,011, filed on Feb. 2, 2017, now Pat. No. 10,478,410, which is a continuation of application No. 14/849,981, filed on Sep. 10, 2015, now Pat. No. 9,593,066, which is a division of application No. 13/933,623, filed on Jul. 2, 2013, now Pat. No. 9,156,786, which is a continuation of application No. 13/548,446, filed on Jul. 13, 2012, now Pat. No. 8,497,393, which is a continuation of application No. 12/334,731, filed on Dec. 15, 2008, now Pat. No. 8,242,305.

(60) Provisional application No. 61/014,232, filed on Dec. 17, 2007.

(51) Int. Cl.

| | |
|---|---|
| ***C07C 405/00*** | (2006.01) |
| ***C07C 39/12*** | (2006.01) |
| ***C07C 39/17*** | (2006.01) |
| ***C07C 51/08*** | (2006.01) |
| ***C07C 51/41*** | (2006.01) |
| ***C07C 59/60*** | (2006.01) |
| ***C07C 59/72*** | (2006.01) |
| ***C07C 213/08*** | (2006.01) |
| ***C07C 253/00*** | (2006.01) |
| *A01N 37/10* | (2006.01) |

(52) U.S. Cl.

CPC ............ *C07C 405/00* (2013.01); *C07C 51/08* (2013.01); *C07C 51/41* (2013.01); *C07C 51/412* (2013.01); *C07C 59/72* (2013.01); *C07C 213/08* (2013.01); *C07C 253/00* (2013.01); *C07C 405/0075* (2013.01); *A01N 37/10* (2013.01); *C07C 39/12* (2013.01); *C07C 39/17* (2013.01); *C07C 59/60* (2013.01); *C07C 2603/12* (2017.05)

(58) Field of Classification Search

CPC ....... C07C 405/00; C07C 51/08; C07C 51/41; C07C 51/412; C07C 59/72; C07C 213/08; C07C 253/00; C07C 405/0075; C07C 39/12; C07C 39/17; C07C 59/60; C07C 2603/12; C07C 59/62; A01N 37/10; A61P 1/00; A61P 1/14; A61P 7/02; A61P 9/00; A61P 9/12; A61P 11/00; A61P 11/06; A61P 35/00; A61K 31/191

USPC .......................................................... 514/569

See application file for complete search history.

(56) References Cited

U.S. PATENT DOCUMENTS

| | | | |
|---|---|---|---|
| 3,703,544 | A | 11/1972 | Morozowich |
| 3,888,916 | A | 6/1975 | Sinkula |
| 4,306,075 | A | 12/1981 | Aristoff |
| 4,306,076 | A | 12/1981 | Nelson |
| 4,424,376 | A | 1/1984 | Moniot et al. |
| 4,434,164 | A | 2/1984 | Lombardino |
| 4,463,183 | A | 7/1984 | Haslanger |
| 4,486,598 | A | 12/1984 | Aristoff |
| 4,544,764 | A | 10/1985 | Aristoff |
| 4,668,814 | A | 5/1987 | Aristoff |
| 4,683,330 | A | 7/1987 | Aristoff |
| 5,153,222 | A | 10/1992 | Tadepalli et al. |
| 5,466,713 | A | 11/1995 | Blitstein-Willinger et al. |
| 5,506,265 | A | 4/1996 | Blitstein-Willinger |
| 6,054,486 | A | 4/2000 | Crow et al. |
| 6,441,245 | B1 | 8/2002 | Moriarty et al. |
| 6,521,212 | B1 | 2/2003 | Cloutier et al. |
| 6,528,688 | B2 | 3/2003 | Moriarty et al. |
| 6,700,025 | B2 | 3/2004 | Moriarty et al. |
| 6,706,283 | B1 | 3/2004 | Appel et al. |
| 6,756,033 | B2 | 6/2004 | Cloutier et al. |

(Continued)

FOREIGN PATENT DOCUMENTS

| | | | |
|---|---|---|---|
| CA | 2710726 | A1 | 1/2012 |
| CN | 101891596 | A | 11/2010 |

(Continued)

OTHER PUBLICATIONS

Alexander et al., "The Synthesis of Benzindene Prostacyclin Analogs as Potential Antiulcer Agents," Prostaglandins, 1986, 32(5):647-653.

(Continued)

*Primary Examiner* — Yevgeny Valenrod
(74) *Attorney, Agent, or Firm* — Foley & Lardner LLP

(57) ABSTRACT

This present invention relates to an improved process to prepare prostacyclin derivatives. One embodiment provides for an improved process to convert benzindene triol to treprostinil via salts of treprostinil and to purify treprostinil.

10 Claims, No Drawings

(56) References Cited

U.S. PATENT DOCUMENTS

| | | | |
|---|---|---|---|
| 6,765,117 | B2 | 7/2004 | Moriarty et al. |
| 6,803,386 | B2 | 10/2004 | Shorr et al. |
| 6,809,223 | B2 | 10/2004 | Moriarty et al. |
| 7,199,157 | B2 | 4/2007 | Wade et al. |
| 7,384,978 | B2 | 6/2008 | Phares et al. |
| 7,417,070 | B2 | 8/2008 | Phares et al. |
| 8,242,305 | B2 | 8/2012 | Batra et al. |
| 8,497,393 | B2 | 7/2013 | Batra et al. |
| 9,593,066 | B2 | 3/2017 | Batra et al. |
| 9,604,901 | B2 | 3/2017 | Batra et al. |
| 2001/0038855 | A1 | 11/2001 | Desjardin et al. |
| 2001/0056095 | A1 | 12/2001 | Mylari |
| 2002/0173672 | A1 | 11/2002 | Moriarty et al. |
| 2004/0176645 | A1 | 9/2004 | Moriarty et al. |
| 2005/0085540 | A1 | 4/2005 | Phares et al. |
| 2005/0101608 | A1 | 5/2005 | Santel |
| 2005/0165111 | A1 | 7/2005 | Wade et al. |
| 2005/0282901 | A1 | 12/2005 | Phares et al. |
| 2005/0282903 | A1 | 12/2005 | Wade et al. |
| 2007/0078095 | A1 | 4/2007 | Phares et al. |
| 2007/0078182 | A1 | 4/2007 | Phares et al. |
| 2008/0200449 | A1 | 8/2008 | Olschewski et al. |
| 2008/0249167 | A1 | 10/2008 | Phares et al. |
| 2008/0280986 | A1 | 11/2008 | Wade et al. |
| 2009/0036465 | A1 | 2/2009 | Roscigno et al. |
| 2009/0163738 | A1 | 6/2009 | Batra et al. |

FOREIGN PATENT DOCUMENTS

| | | | |
|---|---|---|---|
| CN | 101891715 | A | 11/2010 |
| EP | 0 004 335 | A2 | 10/1979 |
| EP | 0 872 37 | B1 | 8/1983 |
| EP | 0 159 784 | B1 | 10/1985 |
| EP | 0 175 450 | B1 | 3/1986 |
| EP | 0 496 548 | A1 | 7/1992 |
| JP | 56-122328 | A | 9/1981 |
| JP | 59-044340 | A | 3/1984 |
| WO | WO-98/18452 | A1 | 5/1998 |
| WO | WO-98/39337 | A1 | 9/1998 |
| WO | WO-99/21830 | A1 | 5/1999 |
| WO | WO-03/070163 | A2 | 8/2003 |
| WO | WO-2005/007081 | A2 | 1/2005 |
| WO | WO-2007/134292 | A2 | 11/2007 |
| WO | WO-2008/100977 | A2 | 8/2008 |
| WO | WO-2009/117095 | A1 | 9/2009 |
| WO | WO-2012/009816 | A1 | 1/2012 |

OTHER PUBLICATIONS

Aristoff et al., "Synthesis and Structure-Activity Relationship of Novel Stable Prostacyclin Analogs," Advances in Prostaglandin, Thromboxane, and Leukotriene Research, 1983, 11:267-274.

Aristoff et al., "Total Synthesis of a Novel Antiulcer Agent via a Modification of the Intramolecular Wadsworth-Emons-Wittig Reaction," J. Am. Chem. Soc., 1985, 107:7967-7974.

Aristoff et al., "Synthesis of Benzopyran Prostaglandins, Potent Stable Prostacyclin Analogs, Via an Intramolecular Mistunobu Reaction," Tetrahedron Letters, 1984, 25(36):3955-3958.

Arumugan et al., "A New Purification Process for Pharmaceutical and Chemical Industries," Organic Process Research & Development, 2005, 9:319-320.

Batra et al., "Crystallization Process Development for a Stable Polymorph of Treprostinil Diethanolamine (UT-15C) by Seeding," Organic Process Research & Development, 2009, 13:242-249.

Belch et al., "Randomized, Double-Blind, Placebo-Controlled Study Evaluating the Efficacy and Safety of AS-013, a Prostaglandin E1 Prodrug, in Patients with Intermittent Claudication," Circulation, May 6, 1997, 95(9):2298-2302.

Bighley et al., "Salt Forms of Drugs and Absorption," Encyclopedia of Pharmaceutical Technology, Swarbrick et al., Eds., 1995, 13:453-499.

Burk et al., "An Enantioselective Synthesis of (S)-(+)-3-Aminomethyl-5-methylhexanoic Acid via Asymmetric Hydrogenation," J. Org. Chem., 2003, 68:5731-5734.

Chemburkar et al., "Dealing with the Impact of Ritonavir Polymorphs on the Late Stages of Bulk Drug Process Development", Organic Process Research & Development, 2000, 4:413-417.

Chung et al., "Promoters for the (Alkyne)hexacarbonyldicobalt-Based Cyclopentenone Synthesis," Organometallics, 1993, 12:220-223.

Clark et al., "High-Performance Liquid Chromatographic Method for Determining the Enantiomeric Purity of a Benzindene Prostaglandin by a Diastereomeric Separation," Journal of Chromatography, 1987, 408:275-283.

Decision Redacted Institute of Inter Partes Review dated Nov. 23, 2016, in *Steadymed Ltd.* (Petitioner), v. *United Therapeutics Corporation* (Patent Owner), Case IPR2016-00006, U.S. Pat. No. 8,497,393, 53 pages.

Defendant Actavis Laboratories FL, Inc. Preliminary Invalidity Contentions, dated Aug. 30, 2016, *United Therapeutics Corporation, and Supernus Pharmaceuticals, Inc.*, (Plaintiff) v. *Actavis Laboratories FL, Inc.*, (Defendant), in The United States District Court for the Distrito of New Jersey, Civil Action No. 3:16-cv-01816-PGS-LHG, Civil Action No. 3:16-cv-03642-PGS-LHG, 330 pages (see particularly pp. 18-20, 42-62 and 269-280).

Defendant Sandoz Inc.'s Invalidity Contention Chartss dated Feb. 5, 2015, *United Therapeutics Corporation* (Plaintiff) v. *Sandoz Inc.* (Defendant), in The United States District Court for the District of New Jersey, Civil Action No. 3:14-cv-5499(PGH)(LHG), 189 pages.

Defendant Teva Pharmaceuticals USA, Inc.'s Amended Non-Infringement and Invalidity Contentions, dated Apr. 24, 2015, *United Therapeutics Corporation* (Plaintiff) v. *Teva Pharmaceuticals USA, Inc.* (Defendant), in The United States District Court for the District of New Jersey, Civil Action No. 3:14-cv-05498(PGS)(LHG), 94 pages, (see particularly pp. 22-54).

Ege, S., Organic Chemistry Second Edition, 1989, 541-547.

Eliel et al., Stereochemistry of Organic Compounds, 1994, 322-325.

Exhibit G, Invalidity Claim Chart for the '393 patent, Jan. 12, 2015, 66 pages.

Final Written Decision dated Mar. 31, 2017, in *Steadymed Ltd.* (Petitioner) v. *United Therapeutics Corporation* (Patent Owner), Case IPR2016-00006, U.S. Pat. No. 8,497,393, 91 pages.

Hardinger et al., "Triply-Convergent Syntheses of Two Homochiral Arene-Fused Prostacyclin Analogs Related to U68,215," Bioorganic & Medicinal Chemistry Letters, 1991, 1(1):79-82.

Harwood et al., Experimental organic chemistry: Principles and Practice, 1989, 127-134.

Hicks et al., "A Practical Titanium-Catalyzed Synthesis of Bicyclic Cyclopentenones and Allylic Amines," J. Org. Chem., 1996, 61:2713-2718.

IPR2020-00769, Petition for Inter Partes Review of U.S. Pat. No. 9,593,066, *Liquidia Technologies, Inc.* (Petitioner) v. *United Therapeutics Corporation* (Patent Owner), Mar. 30, 2020, 79 pages, and Exhibits 1002, 1003, 1012 and 1015.

IPR2020-00770, Petition for Inter Partes Review of U.S. Pat. No. 9,604,901, *Liquidia Technologies, Inc.* (Petitioner) v. *United Therapeutics Corporation* (Patent Owner), Mar. 30, 2020, 82 pages, and Exhibits 1002 and 1015.

Jeong et al., "Catalytic Version of the Intramolecular Pauson-Khand Reaction," J. Am. Chem. Soc., 1994, 116:3159-3160.

Jones, Maitland Jr., Organic Chemistry, 2nd Ed., 2000, 153-155.

Khand et al., "Organocobalt Complexes. Part II. Reaction of Acetylenehexacarbonyl-dicobalt Complexes, (R1C2R2)Co2(CO)6, with Norbornene and its Derivatives," J. Chem. Soc., J.C.S. Perkin I., 1973, 977-981.

Li & Liu, "Synthetic Approaches to the 2002 New Drugs," Mini-Reviews in Medicinal Chemistry, 2004, 4, 207-233.

Lin et al., "Benzindene Prostaglandins. Synthesis of Optically Pure 15-Deoxy-U-68,215 and Its Enantiomer via a Modified Intramolecular Wadsworth-Emmons-Wittig Reaction," J. Org. Chem., 1987, 52:5594-5601.

Mathre et al., "A Practical Enantioselective Synthesis of a,a-Diaryl-2-pyrrolidinemethanol. Preparation and Chemistry of the Corresponding Oxazaborolidines," J. Org. Chem., 1991, 56:751- 762.

(56) References Cited

OTHER PUBLICATIONS

McManus et al., "Tetrazole Analogs of Plant Auxins," J. Org. Chem., 1959, 24:1464-1467.
Monson, Richard S., Advanced Organic Synthesis, Methods and Techniques, 1971, 178-188.
Moriarty et al., "The Intramolecular Asymmetric Pauson-Khand Cyclization as a Novel and General Stereoselective Route to Benzindene Prostacyclins: Synthesis of UT-15 (Treprostinil)," J. Org. Chem. 2004, 69, 1890-1902.
Mulzer et al., "Asymmetric Synthesis of Carbacyclin Precursors by Pauson-Khand Cyclization," Liebigs Ann. Chem., 1988: 891-897.
Nelson, Norman A., "Prostaglandin Nomenclature," J. Med. Chem., Sep. 1974, 17(9):911-918.
Notice of Final Rule of Aug. 14, 2012, 77 Federal Register 48612.01.
Ohno et al., "Development of Dual-Acting Benzofurans for Thromboxane A2 Receptor Antagonist and Prostacyclin Receptor Agonist: Synthesis, Structure-Activity Relationship, and Evaluation of Benzofuran Derivatives," J. Med. Chem., 2005, 48:5279-5294.
Olmsted III et al., Chemistry, The Molecular Science, Mosby-Year Book, Inc., Chapter 10 "Effects of Intermolecular Forces," 1994, 428-486.
Pagenkopf et al., "Photochemical Promotion of the Intramolecular Pauson-Khand Reaction. A New Experimental Protocol for Cobalt-Catalyzed [2+2+1] Cycloadditions," J. Am. Chem. Soc., 1996, 118:2285-2286.
Pagenkopf, Brian L., "Substrate and Reagent Control of Diastereoselectivity in Transition Metal? Mediated Process: Development of a Catalytic Photo Promoted Pauson-Khand Reaction," Diss. Abstr. Int., 1977, 57(12), abstract of pp. 7535-7547.
Patent Owner Demonstratives filed Nov. 23, 2016, in *Steadymed Ltd.* (Petitioner), v. *United Therapeutics Corporation* (Patent Owner), Case IPR2016-00006, U.S. Pat. No. 8,497,393, 62 pages.
Patent Owner Response to Petition filed Nov. 23, 2016, in *Steadymed Ltd.* (Petitioner), v. *United Therapeutics Corporation* (Patent Owner), Case IPR2016-00006, U.S. Pat. No. 8,497,393, with Redacted Exhibits 2006, 2020, 2022, 2058 and 2059 filed Nov. 23, 2016, 1151 pages.
Patterson et al., "Acute Hemodynamic Effects of the Prostacyclin Analog 15AU81 in Severe Congestive Heart Failure," Am. J. Cardio., 1995, 75:26A-33A.
Paulson, Peter L., "The Khand Reaction," Tetrahedron, 1985, 41(24):5855-5860.
Pavia et al., Introduction to Organic Laboratory Techniques, First Edition, 1998, 648.
Petitioner's Demonstratives filed Nov. 28, 2016, in *Steadymed Ltd.* (Petitioner), v. *United Therapeutics Corporation* (Patent Owner), Case IPR2016-00006, U.S. Pat. No. 8,497,393.
Physicians' Desk Reference, 59 Edition, 2005, for Bicillin® L-A (penicillin G benzathine suspension), 5 pages.
Priscinzano et al., "Piperidine Analogues of 1-[2-[Bis(4-fluorophenyl)methoxy]ethyl]-4-(3-phenylpropyl)piperazine (GBR 12909): High Affinity Ligands for the Dopamine Transporter," J. Med. Chem., 2002, 45:4371-4374.
Redacted Defendant Sandoz Inc.'s Invalidity Contentions dated Feb. 5, 2015, *United Therapeutics Corporation* (Plaintiff) v. *Sandoz Inc.* (Defendant), in The United States District Court for the District of New Jersey, Civil Action No. 3:14-cv-5499(PGH)(LHG), 90 pages.
Redacted Defendant Watson Laboratories, Inc.'s Invalidity Contentions dated Dec. 11, 2015, *United Therapeutics Corporation* (Plaintiff) v. *Watson Laboratories, Inc.* (Defendant), in The United States District Court for the District of New Jersey, Civil Action No. 3:15-cv-05723-PGS-LHG, 35 pages.
Redacted Petitioner's Reply to Patent Owner's Response to Petition filed on Sep. 27, 2016 in *Steadymed Ltd.* (Petitioner), v. *United Therapeutics Corporation* (Patent Owner), Case IPR2016-00006, U.S. Pat. No. 8,497,393, with Exhibits 1022-1028.
Remodulin (Treprostinil Sodium Salt) Label dated May 21, 2002.
Remodulin® label, 2014, 17 pages.
Schoffstall et al., Microscale and Miniscale Organic Chemistry Laboratory Experiments, 2nd. Ed., 2004, 200-202.
Schoffstall, et al., Microscale and Miniscale Organic Chemistry Laboratory Experiments, 2004, 2nd Ed., 200-202.
Schore, "Transition-Metal-Mediated Cycloaddition Reactions of Alkynes in Organic Synthesis," Chem. Rev., 1988, 88:1081-1119.
Service Third Party Submission dated Oct. 16, 2016, filed but not entered in U.S. Appl. No. 14/849,981 on Oct. 16, 2016, with 6 indicated attachments, 822 pages.
Shambayati et al., "N-Oxide Promjoted Pauson-Khand Cyclizations at Room Temperature," Tetrahedron Letters, 1990, 31(37):5289-5292.
Simonneau et al., "Continuous Subcutaneous Infusion of Treprostinil, a Prostacyclin Analogue, in Patients with Pulmonary Arterial Hypertension," Am. J. Respir. Crit. Care Med., 2002, 165:800-804.
Snell et al., "Investigating the Effect of Impurities on Macromolecule Crystal Growth in Microgravity," Crystal Growth & Design, 2001, 1(2):151-158.
Sorbera et al., "UT-15. Treatment of Pulmonary Hypertension Treatment of Peripheral Vascular Disease," Drug of the Future, 2001, 26(4):364-374.
Sorrell, Thomas N., Organic Chemistry, 1999, 755-758.
*Steadymed Ltd.*, v. *United Therapeutics Corporation*, Petition for Inter Partes Review of U.S. Pat. No. 8,497,393, under 37 CFR 42.100, dated Oct. 1, 2015, with Exhibits 1009, 1010, 1017 and 1018.
Takano et al., "Enantiodivergent Synthesis of Both Enantiomers of Sulcatol and Matsutake Alcohol from (R)-Epichlorohydrin," Chemistry Letters, 1987:2017-2020.
Text of 37 CFR 42.73 concerning estoppel.
Viedma, Cristobal, "Selective Chiral Symmetry Breaking during Crystallization: Parity Violation of Cryptochiral Environment in Control?" Crystal Growth & Design, 2007, 7(3):553-556.
Whittle et al., "Antithrombotic Assessment and Clinical Potential of Prostacyclin Analogues," Progress in Medicinal Chemistry, Ellis et al. Eds., 1984, 21:238-279.
Wiberg, Kenneth, Laboratory Technique in Organic Chemistry, 1960, 112.
Yu et al., "Novel Synthetic Route of a Pivotal Intermediate for the Synthesis of 1β-Methyl Carbapenem Antibiotics," Organic Process Research & Development, 2006, 10:829-832.
Zhang et al., "A Nickel(0)-Catalyzed Process for the Transformation of Enynes to Bicyclic Cyclopentenones," J. Org. Chem., 1996, 61:4498-4499.
Decision dated Jul. 24, 2023, CAFC 2022-2217, CAFC 2023-1021, *United Therapeutics Corporation* (Plaintiff-Cross-Appellant) v. *Liquidia Technologies, Inc.* (Defendant-Appellant), Appeals from the U.S. District Court for the District of Delaware in No. 1:20-cv-00755-RGA-JLH, 23 pages.
Defendant's Post-Trial Opening Brief Regarding Invalidity of U.S. Pat. Nos. 9,593,066 and 10,716,893, filed May 4, 2022, in Civil Action No. 20-755-RGA, *United Therapeutics Corporation* (Plaintiff) v. *Liquidia Technologies, Inc.* (Defendant), 85 pages.
Trial Opinion dated Aug. 31, 2023 in Civil Action No. 20-755-RGA, *United Therapeutics Corporation* (Plaintiff) v. *Liquidia Technologies, Inc.* (Defendant), 29 pages.

PROCESS TO PREPARE TREPROSTINIL, THE ACTIVE INGREDIENT IN REMODULIN®

CROSS-REFERENCE TO RELATED APPLICATIONS

This application is a Continuation of U.S. application Ser. No. 16/594,737, filed Oct. 7, 2019, which is a Continuation of U.S. application Ser. No. 15/423,011, filed Feb. 2, 2017, which is a Continuation of U.S. application Ser. No. 14/849,981, filed Sep. 10, 2015, which is a Divisional of U.S. application Ser. No. 13/933,623, filed Jul. 2, 2013, which is a Continuation of U.S. application Ser. No. 13/548,446, filed Jul. 13, 2012, which is a Continuation of U.S. application Ser. No. 12/334,731, filed Dec. 15, 2008, which claims priority from U.S. Provisional Patent Application 61/014,232, filed Dec. 17, 2007, the entire contents of which are incorporated herein by reference.

BACKGROUND

The present invention relates to a process for producing prostacyclin derivatives and novel intermediate compounds useful in the process.

Prostacyclin derivatives are useful pharmaceutical compounds possessing activities such as platelet aggregation inhibition, gastric secretion reduction, lesion inhibition, and bronchodilation.

Treprostinil, the active ingredient in Remodulin, was first described in U.S. Pat. No. 4,306,075. Treprostinil, and other prostacyclin derivatives have been prepared as described in Moriarty, et al in *J. Org. Chem.* 2004, 69, 1890-1902, *Drug of the Future,* 2001, 26(4), 364-374, U.S. Pat. Nos. 6,441,245, 6,528,688, 6,765,117 and 6,809,223. Their teachings are incorporated by reference to show how to practice the embodiments of the present invention.

U.S. Pat. No. 5,153,222 describes use of treprostinil for treatment of pulmonary hypertension. Treprostinil is approved for the intravenous as well as subcutaneous route, the latter avoiding septic events associated with continuous intravenous catheters. U.S. Pat. Nos. 6,521,212 and 6,756,033 describe administration of treprostinil by inhalation for treatment of pulmonary hypertension, peripheral vascular disease and other diseases and conditions. U.S. Pat. No. 6,803,386 discloses administration of treprostinil for treating cancer such as lung, liver, brain, pancreatic, kidney, prostate, breast, colon and head-neck cancer. U.S. patent application publication No. 2005/0165111 discloses treprostinil treatment of ischemic lesions. U.S. Pat. No. 7,199,157 discloses that treprostinil treatment improves kidney functions. U.S. patent application publication No. 2005/0282903 discloses treprostinil treatment of neuropathic foot ulcers. U.S. application Ser. No. 12/028,471 filed Feb. 8, 2008, discloses treprostinil treatment of pulmonary fibrosis. U.S. Pat. No. 6,054,486 discloses treatment of peripheral vascular disease with treprostinil. U.S. patent application Ser. No. 11/873,645 filed Oct. 17, 2007 discloses combination therapies comprising treprostinil. U.S. publication No. 2008/0200449 discloses delivery of treprostinil using a metered dose inhaler. U.S. publication No. 2008/0280986 discloses treatment of interstitial lung disease with treprostinil. U.S. application Ser. No. 12/028,471 filed Feb. 8, 2008 discloses treatment of asthma with treprostinil. U.S. Pat. Nos. 7,417,070, 7,384,978 and U.S. publication Nos. 2007/0078095, 2005/0282901, and 2008/0249167 describe oral formulations of treprostinil and other prostacyclin analogs.

Because Treprostinil, and other prostacyclin derivatives are of great importance from a medicinal point of view, a need exists for an efficient process to synthesize these compounds on a large scale suitable for commercial production.

SUMMARY

The present invention provides in one embodiment a process for the preparation of a compound of formula I, hydrate, solvate, prodrug, or pharmaceutically acceptable salt thereof.

(I)

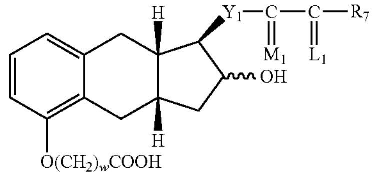

The process comprises the following steps:

(a) alkylating a compound of structure II with an alkylating agent to produce a compound of formula III, (II)

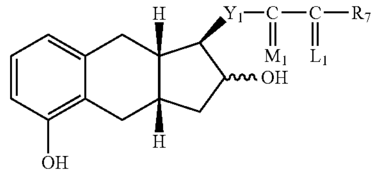

(III)

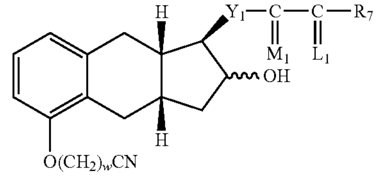

wherein w=1, 2, or 3;

$Y_1$ is trans-CH═CH—, cis-CH═CH—, —$CH_2(CH_2)_m$—, or —C≡C—; m is 1, 2, or 3;

$R_7$ is (1) —$C_pH_{2p}$—$CH_3$, wherein p is an integer from 1 to 5, inclusive, (2) phenoxy optionally substituted by one, two or three chloro, fluoro, trifluoromethyl, ($C_1$-$C_3$) alkyl, or ($C_1$-$C_3$)alkoxy, with the proviso that not more than two substituents are other than alkyl, with the proviso that $R_7$ is phenoxy or substituted phenoxy, only when $R_3$ and $R_4$ are hydrogen or methyl, being the same or different, (3) phenyl, benzyl, phenylethyl, or phenylpropyl optionally substituted on the aromatic ring by one, two or three chloro, fluoro, trifluoromethyl, ($C_1$-$C_3$) alkyl, or ($C_1$-$C_3$)alkoxy, with the proviso that not more than two substituents are other than alkyl, (4) cis-CH═CH—$CH_2$—$CH_3$, (5) —$(CH_2)_2$—CH(OH)—$CH_3$, or (6) —$(CH_2)_3$—CH═C$(CH_3)_2$;

wherein —C($L_1$)-$R_7$ taken together is (1) ($C_4$-$C_7$)cycloalkyl optionally substituted by 1 to 3 ($C_1$-$C_5$)alkyl;

(2) 2-(2-furyl)ethyl, (3) 2-(3-thienyl)ethoxy, or (4) 3-thienyloxymethyl;

$M_1$ is α-OH:β-$R_5$ or α-$R_5$:β-OH or α-O$R_2$:β-$R_5$ or α-$R_5$:β-O$R_2$, wherein $R_5$ is hydrogen or methyl, $R_2$ is an alcohol protecting group, and $L_1$ is α-$R_3$:β-$R_4$, α-$R_4$:β-$R_3$, or a mixture of α-$R_3$:β-$R_4$ and α-$R_4$:β-$R_3$, wherein $R_3$ and $R_4$ are hydrogen, methyl, or fluoro, being the same or different, with the proviso that one of $R_3$ and $R_4$ is fluoro only when the other is hydrogen or fluoro.

(b) hydrolyzing the product of step (a) with a base, (c) contacting the product of step (b) with a base B to for a salt of formula $I_s$ ($I_s$)

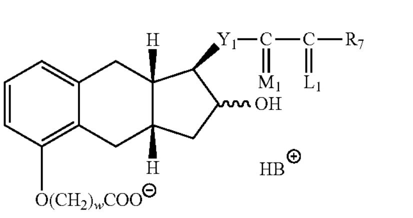

(d) reacting the salt from step (c) with an acid to form the compound of formula I.

The present invention provides in another embodiment a process for the preparation of a compound of formula IV.

(IV)

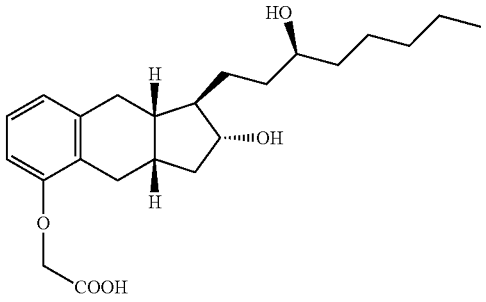

The process comprises the following steps:

(a) alkylating a compound of structure V with an alkylating agent to produce a compound of formula VI, (V)

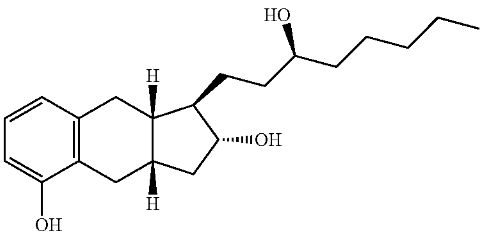

-continued (VI)

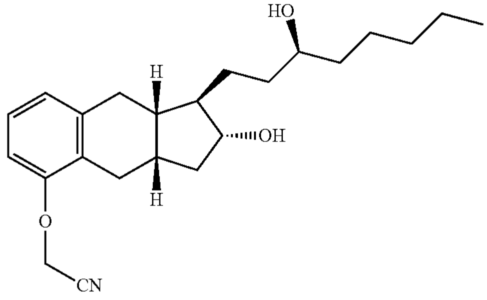

(b) hydrolyzing the product of step (a) with a base, (c) contacting the product of step (b) with a base B to for a salt of formula $IV_s$, and ($IV_s$)

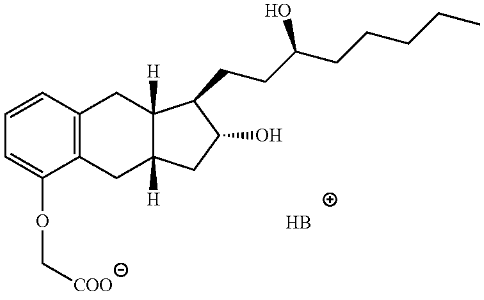

(d) reacting the salt from step (b) with an acid to form the compound of formula IV.

DETAILED DESCRIPTION

The various terms used, separately and in combinations, in the processes herein described are defined below.

The expression "comprising" means "including but not limited to." Thus, other non-mentioned substances, additives, carriers, or steps may be present. Unless otherwise specified, "a" or "an" means one or more.

$C_{1-3}$-alkyl is a straight or branched alkyl group containing 1-3 carbon atoms. Exemplary alkyl groups include methyl, ethyl, n-propyl, and isopropyl.

$C_{1-3}$-alkoxy is a straight or branched alkoxy group containing 1-3 carbon atoms. Exemplary alkoxy groups include methoxy, ethoxy, propoxy, and isopropoxy.

$C_{4-7}$-cycloalkyl is an optionally substituted monocyclic, bicyclic or tricyclic alkyl group containing between 4-7 carbon atoms. Exemplary cycloalkyl groups include but not limited to cyclobutyl, cyclopentyl, cyclohexyl, and cycloheptyl.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein.

As used herein, the term "prodrug" means a derivative of a compound that can hydrolyze, oxidize, or otherwise react under biological conditions (in vitro or in vivo) to provide an active compound. Examples of prodrugs include, but are not limited to, derivatives of a compound that include biohydrolyzable groups such as biohydrolyzable amides, biohydrolyzable esters, biohydrolyzable carbamates, biohydrolyzable carbonates, biohydrolyzable ureides, and biohydrolyzable phosphate analogues (e.g., monophosphate, diphosphate or triphosphate).

As used herein, "hydrate" is a form of a compound wherein water molecules are combined in a certain ratio as an integral part of the structure complex of the compound.

As used herein, "solvate" is a form of a compound where solvent molecules are combined in a certain ratio as an integral part of the structure complex of the compound.

"Pharmaceutically acceptable" means in the present description being useful in preparing a pharmaceutical composition that is generally safe, non-toxic and neither biologically nor otherwise undesirable and includes being useful for veterinary use as well as human pharmaceutical use.

"Pharmaceutically acceptable salts" mean salts which are pharmaceutically acceptable, as defined above, and which possess the desired pharmacological activity. Such salts include acid addition salts formed with organic and inorganic acids, such as hydrogen chloride, hydrogen bromide, hydrogen iodide, sulfuric acid, phosphoric acid, acetic acid, glycolic acid, maleic acid, malonic acid, oxalic acid, methanesulfonic acid, trifluoroacetic acid, fumaric acid, succinic acid, tartaric acid, citric acid, benzoic acid, ascorbic acid and the like. Base addition salts may be formed with organic and inorganic bases, such as sodium, ammonia, potassium, calcium, ethanolamine, diethanolamine, N-methylglucamine, choline and the like. Included in the invention are pharmaceutically acceptable salts or compounds of any of the formulae herein.

Depending on its structure, the phrase "pharmaceutically acceptable salt," as used herein, refers to a pharmaceutically acceptable organic or inorganic acid or base salt of a compound. Representative pharmaceutically acceptable salts include, e.g., alkali metal salts, alkali earth salts, ammonium salts, water-soluble and water-insoluble salts, such as the acetate, amsonate (4,4-diaminostilbene-2, 2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

The present invention provides for a process for producing treprostinil and other prostacyclin derivatives and novel intermediate compounds useful in the process. The process according to the present invention provides advantages on large-scale synthesis over the existing method. For example, the purification by column chromatography is eliminated, thus the required amount of flammable solvents and waste generated are greatly reduced. Furthermore, the salt formation is a much easier operation than column chromatography. Moreover, it was found that the product of the process according to the present invention has higher purity. Therefore the present invention provides for a process that is more economical, safer, faster, greener, easier to operate, and provides higher purity.

One embodiment of the present invention is a process for the preparation of a compound of formula I, or a hydrate, solvate, prodrug, or pharmaceutically acceptable salt thereof.

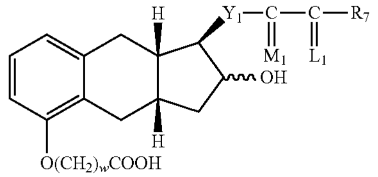

(I)

The process comprises the following steps:

(a) alkylating a compound of formula II with an alkylating agent to produce a compound of formula III,

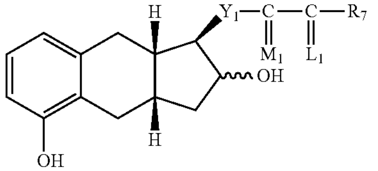

(II)

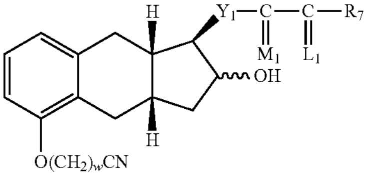

(III)

wherein w=1, 2, or 3;

$Y_1$ is trans-CH=CH—, cis-CH=CH—, —$CH_2(CH_2)_m$—, or —C≡C—; m is 1, 2, or 3;

$R_7$ is (1) —$C_pH_{2p}$—$CH_3$, wherein p is an integer from 1 to 5, inclusive, (2) phenoxy optionally substituted by one, two or three chloro, fluoro, trifluoromethyl, ($C_1$-$C_3$) alkyl, or ($C_1$-$C_3$)alkoxy, with the proviso that not more than two substituents are other than alkyl, with the proviso that $R_7$ is phenoxy or substituted phenoxy, only when $R_3$ and $R_4$ are hydrogen or methyl, being the same or different, (3) phenyl, benzyl, phenylethyl, or phenylpropyl optionally substituted on the aromatic ring by one, two or three chloro, fluoro, trifluoromethyl, ($C_1$-$C_3$) alkyl, or ($C_1$-$C_3$)alkoxy, with the proviso that not more than two substituents are other than alkyl, (4) cis-CH=CH—$CH_2$—$CH_3$, (5) —$(CH_2)_2$—CH(OH)—$CH_3$, or (6) —$(CH_2)_3$—CH=$C(CH_3)_2$;

wherein —C($L_1$)-$R_7$ taken together is (1) ($C_4$-$C_7$)cycloalkyl optionally substituted by 1 to 3 ($C_1$-$C_5$)alkyl;

(2) 2-(2-furyl)ethyl, (3) 2-(3-thienyl)ethoxy, or (4) 3-thienyloxymethyl;

$M_1$ is α-OH:β-$R_5$ or α-$R_5$:β-OH or α-$OR_2$:β-$R_5$ or α-$R_5$:β-$OR_2$, wherein $R_5$ is hydrogen or methyl, $R_2$ is an alcohol protecting group, and $L_1$ is α-$R_3$:β-$R_4$, α-$R_4$:β-$R_3$, or a mixture of α-$R_3$:β-$R_4$ and α-$R_4$:β-$R_3$, wherein $R_3$ and $R_4$ are hydrogen, methyl, or fluoro, being the same or different, with the proviso that one of $R_3$ and $R_4$ is fluoro only when the other is hydrogen or fluoro.

(b) hydrolyzing the product of step (a) with a base, (c) contacting the product of step (b) with a base B to for a salt of formula $I_s$ ($I_s$)

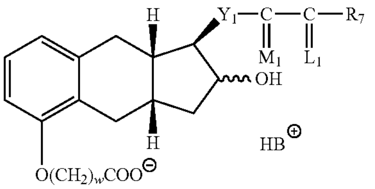

(d) reacting the salt from step (c) with an acid to form the compound of formula I.

In one embodiment, the compound of formula I is at least 90.0%, 95.0%, 99.0%.

The compound of formula II can be prepared from a compound of formula XI, which is a cyclization product of a compound of formula X as described in U.S. Pat. No. 6,441,245.

(X)

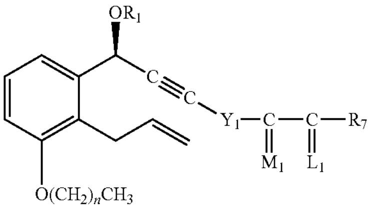

(XI)

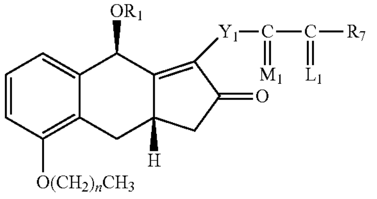

Wherein n is 0, 1, 2, or 3.

The compound of formula II can be prepared alternatively from a compound of formula XIII, which is a cyclization product of a compound of formula XII as described in U.S. Pat. No. 6,700,025.

(XII)

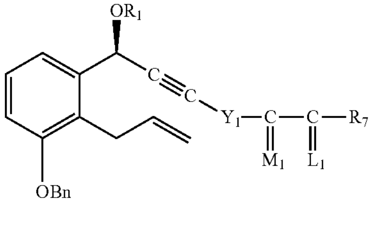

-continued (XIII)

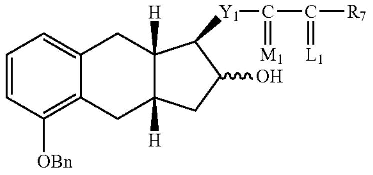

One embodiment of the present invention is a process for the preparation of a compound having formula IV, or a hydrate, solvate, or pharmaceutically acceptable salt thereof.

(IV)

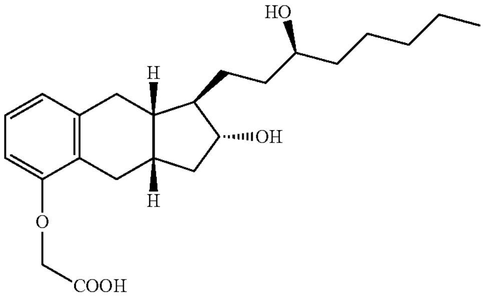

The process comprises (a) alkylating a compound of structure V with an alkylating agent such as $ClCH_2CN$ to produce a compound of formula VI, (V)

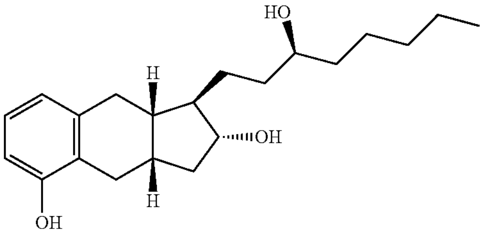

(VI)

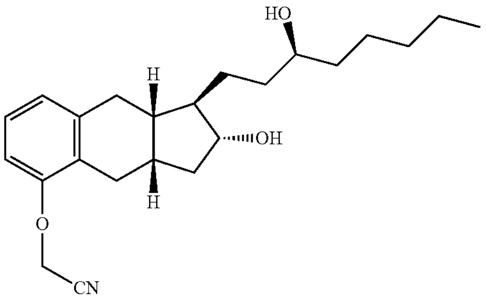

(b) hydrolyzing the product of step (a) with a base such as KOH, (c) contacting the product of step (b) with a base B such as diethanolamine to for a salt of the following structure, and

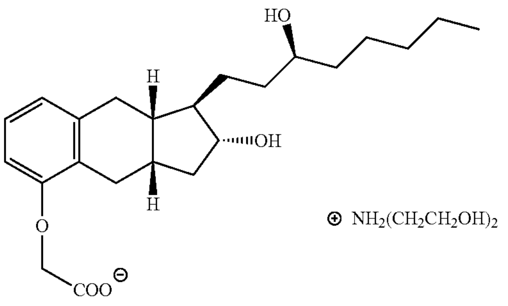

(d) reacting the salt from step (b) with an acid such as HCl to form the compound of formula IV.

In one embodiment, the purity of compound of formula IV is at least 90.0%, 95.0%, 99.0%, 99.5%.

In one embodiment, the process further comprises a step of isolating the salt of formula IVs.

In one embodiment, the base B in step (c) may be ammonia, N-methylglucamine, procaine, tromethanine, magnesium, L-lysine, L-arginine, or triethanolamine.

The following abbreviations are used in the description and/or appended claims, and they have the following meanings:

"MW" means molecular weight.

"Eq." means equivalent.

"TLC" means thin layer chromatography.

"HPLC" means high performance liquid chromatography.

"PMA" means phosphomolybdic acid.

"AUC" means area under curve.

In view of the foregoing considerations, and specific examples below, those who are skilled in the art will appreciate that how to select necessary reagents and solvents in practicing the present invention.

The invention will now be described in reference to the following Examples. These examples are not to be regarded as limiting the scope of the present invention, but shall only serve in an illustrative manner.

EXAMPLES

Example 1. Alkylation of Benzindene Triol

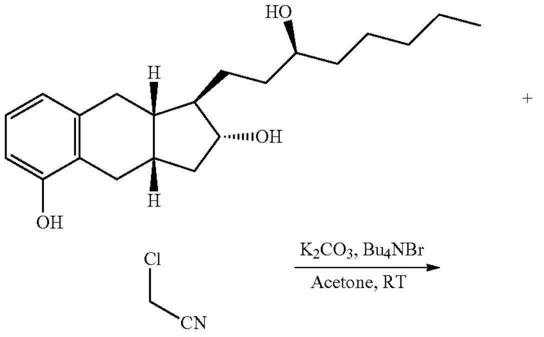

-continued

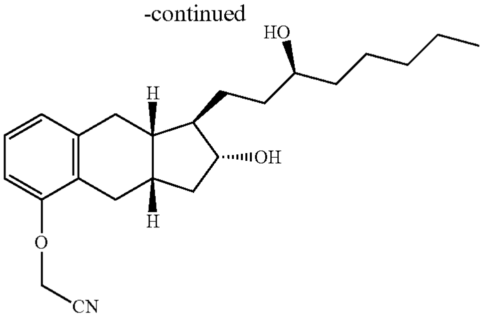

| Name | MW | Amount | Mol. | Eq. |
|---|---|---|---|---|
| Benzindene Triol | 332.48 | 1250 g | 3.76 | 1.00 |
| $K_2CO_3$ (powder) | 138.20 | 1296 g | 9.38 | 2.50 |
| $ClCH_2CN$ | 75.50 | 567 g | 7.51 | 2.0 |
| $Bu_4NBr$ | 322.37 | 36 g | 0.11 | 0.03 |
| Acetone | — | 29 L | — | — |
| Celite ®545 | — | 115 g | — | — |

A 50-L, three-neck, round-bottom flask equipped with a mechanical stirrer and a thermocouple was charged with benzindene triol (1250 g), acetone (19 L) and $K_2CO_3$ (powdered) (1296 g), chloroacetonitrile (567 g), tetrabutylammonium bromide (36 g). The reaction mixture was stirred vigorously at room temperature (23±2° C.) for 16-72 h. The progress of the reaction was monitored by TLC. (methanol/$CH_2Cl_2$; 1:9 and developed by 10% ethanolic solution of PMA). After completion of reaction, the reaction mixture was filtered with/without Celite pad. The filter cake was washed with acetone (10 L). The filtrate was concentrated in vacuo at 50-55° C. to give a light-brown, viscous liquid benzindene nitrile. The crude benzindene nitrile was used as such in the next step without further purification.

Example 2. Hydrolysis of Benzindene Nitrile

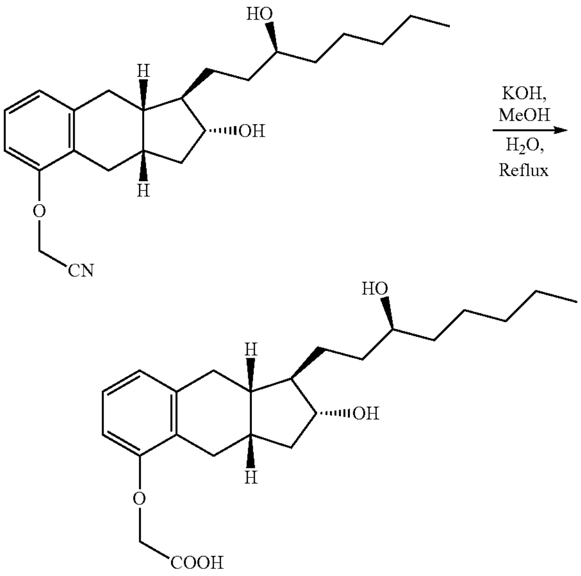

| Name | MW | Amount | Mol. | Eq. |
|---|---|---|---|---|
| Benzindene Nitrile | 371.52 | 1397 g* | 3.76 | 1.0 |
| KOH | 56.11 | 844 g | 15.04 | 4.0 |
| Methanol | — | 12 L | — | — |
| Water | — | 4.25 L | — | — |

*Note:

This weight is based on 100% yield from the previous step. This is not isolated yield.

A 50-L, cylindrical reactor equipped with a heating/cooling system, a mechanical stirrer, a condenser, and a thermocouple was charged with a solution of benzindene nitrile in methanol (12 L) and a solution of KOH (844 g of KOH dissolved in 4.25 L of water). The reaction mixture was stirred and heated to reflux (temperature 72.2° C.). The progress of the reaction was monitored by TLC (for TLC purpose, 1-2 mL of reaction mixture was acidified with 3M HCl to pH 1-2 and extracted with ethyl acetate. The ethyl acetate extract was used for TLC; Eluent: methanol/$CH_2Cl_2$; 1:9, and developed by 10% ethanolic solution of PMA). After completion of the reaction (~5 h), the reaction mixture was cooled to −5 to 10° C. and quenched with a solution of hydrochloric acid (3M, 3.1 L) while stirring. The reaction mixture was concentrated in vacuo at 50-55° C. to obtain approximately 12-14 L of condensate. The condensate was discarded.

The aqueous layer was diluted with water (7-8 L) and extracted with ethyl acetate (2×6 L) to remove impurities soluble in ethyl acetate. To aqueous layer, ethyl acetate (22 L) was added and the pH of reaction mixture was adjusted to 1-2 by adding 3M HCl (1.7 L) with stirring. The organic layer was separated and the aqueous layer was extracted with ethyl acetate (2×11 L). The combined organic layers were washed with water (3×10 L) and followed by washing with a solution of $NaHCO_3$ (30 g of $NaHCO_3$ dissolved in 12 L of water). The organic layer was further washed with saturated solution of NaCl (3372 g of NaCl dissolved in water (12 L)) and dried over anhydrous $Na_2SO_4$ (950-1000 g), once filtered.

The filtrate was transferred into a 72-L reactor equipped with mechanical stirrer, a condenser, and a thermocouple. To the solution of treprostinil in reactor was added activated carbon (110-130 g). The suspension was heated to reflux (temperature 68-70° C.) for at least one hour. For filtration, a pad of Celite® 545 (300-600 g) was prepared in sintered glass funnel using ethyl acetate. The hot suspension was filtered through the pad of Celite® 545. The Celite® 545 was washed with ethyl acetate until no compound was seen on TLC of the washings.

The filtrate (pale-yellow) was reduced to volume of 35-40 L by evaporation in vacuo at 50-55° C. for direct use in next step.

Example 3. Conversion of Treprostinil to Treprostinil Diethanolamine Salt (1:1)

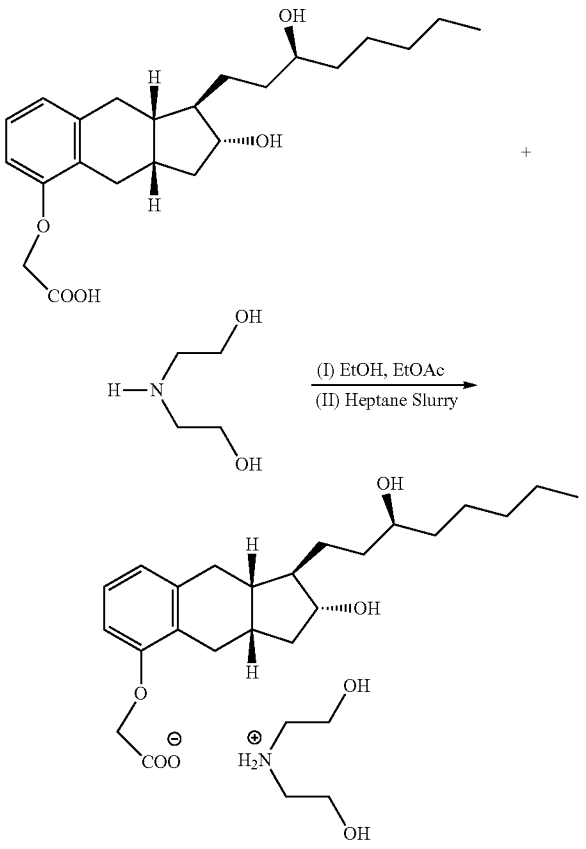

| Name | MW | Amount | Mol | Eq |
|---|---|---|---|---|
| Treprostinil | 390.52 | 1464 g* | 3.75 | 1.0 |
| Diethanolamine | 105.14 | 435 g | 4.14 | 1.1 |
| Ethanol | — | 5.1 L | — | — |
| Ethyl acetate | — | 35 L** | — | — |
| Treprostinil Diethanolamine Salt (seed) | — | 12 g | — | — |

*Note:

This weight is based on 100% yield from benzindene triol. It is not isolated yield. The treprostinil was carried from previous step in ethyl acetate solution and used as such for this step.

**Note:

The total volume of ethyl acetate should be in range of 35-36 L (it should be 7 times the volume of ethanol used). Approximately 35 L of ethyl acetate was carried over from previous step and additional 1.0 L of ethyl acetate was used for rinsing the flask.

A 50-L, cylindrical reactor equipped with a heating/cooling system, a mechanical stirrer, a condenser, and a thermocouple was charged with a solution of treprostinil in ethyl acetate (35-40 L from the previous step), anhydrous ethanol (5.1 L) and diethanolamine (435 g). While stirring, the reaction mixture was heated to 60-75° C., for 0.5-1.0 h to obtain a clear solution. The clear solution was cooled to 55±5° C. At this temperature, the seed of polymorph B of treprostinil diethanolamine salt (~12 g) was added to the clear solution. The suspension of polymorph B was stirred at this temperature for 1 h. The suspension was cooled to 20±2° C. overnight (over a period of 16-24 h). The treprostinil diethanolamine salt was collected by filtration using Aurora filter equipped with filter cloth, and the solid was washed with ethyl acetate (2×8 L). The treprostinil diethanolamine salt was transferred to a HDPE/glass container for air-drying in hood, followed by drying in a vacuum oven at 50±5° C. under high vacuum.

At this stage, if melting point of the treprostinil diethanolamine salt is more than 104° C., it was considered polymorph B. There is no need of recrystallization. If it is less than 104° C., it is recrystallized in EtOH-EtOAc to increase the melting point.

Data on Treprostinil Diethanolamine Salt (1:1)

| Batch No. | Wt. of Benzindene Triol (g) | Wt. of Treprostinil Diethanolamine Salt (1:1) (g) | Yield (%) | Melting point (° C.) |
|---|---|---|---|---|
| 1 | 1250 | 1640 | 88.00 | 104.3-106.3 |
| 2 | 1250 | 1528 | 82.00* | 105.5-107.2 |
| 3 | 1250 | 1499 | 80.42** | 104.7-106.6 |
| 4 | 1236 | 1572 | 85.34 | 105-108 |

*Note:
In this batch, approximately 1200 mL of ethyl acetate solution of treprostinil before carbon treatment was removed for R&D carbon treatment experiments.
**Note:
This batch was recrystallized, for this reason yield was lower.

Example 4. Heptane Slurry of Treprostinil Diethanolamine Salt (1:1)

| Name | Batch No. | Amount | Ratio |
|---|---|---|---|
| Treprostinil Diethanolamine Salt | 1 | 3168 g | 1 |
| Heptane | — | 37.5 L | 12 |
| Treprostinil Diethanolamine Salt | 2 | 3071 g | 1 |
| Heptane | — | 36.0 L | 12 |

A 50-L, cylindrical reactor equipped with a heating/cooling system, a mechanical stirrer, a condenser, and a thermocouple was charged with slurry of treprostinil diethanolamine salt in heptane (35-40 L). The suspension was heated to 70-80° C. for 16-24 h. The suspension was cooled to 22±2° C. over a period of 1-2 h. The salt was collected by filtration using Aurora filter. The cake was washed with heptane (15-30 L) and the material was dried in Aurora filter for 1 h. The salt was transferred to trays for air-drying overnight in hood until a constant weight of treprostinil diethanolamine salt was obtained. The material was dried in oven under high vacuum for 2-4 h at 50-55° C.

Analytical data on and Treprostinil Diethanolamine Salt (1:1)

| Test | Batch 1 | Batch 2 |
|---|---|---|
| IR | Conforms | Conforms |
| Residue on Ignition (ROI) | <0.1% w/w | <0.1% w/w |
| Water content | 0.1% w/w | 0.0% w/w |
| Melting point | 105.0-106.5° C. | 104.5-105.5° C. |
| Specific rotation $[\alpha]^{25}_{589}$ | +34.6° | +35° |
| Organic volatile impurities | | |
| Ethanol | Not detected | Not detected |
| Ethyl acetate | Not detected | <0.05% w/w |
| Heptane | <0.05% w/w | <0.05% w/w |
| HPLC (Assay) | 100.4% | 99.8% |
| Diethanolamine | Positive | Positive |

Example 5. Conversion of Treprostinil Diethanolamine Salt (1:1) to Treprostinil

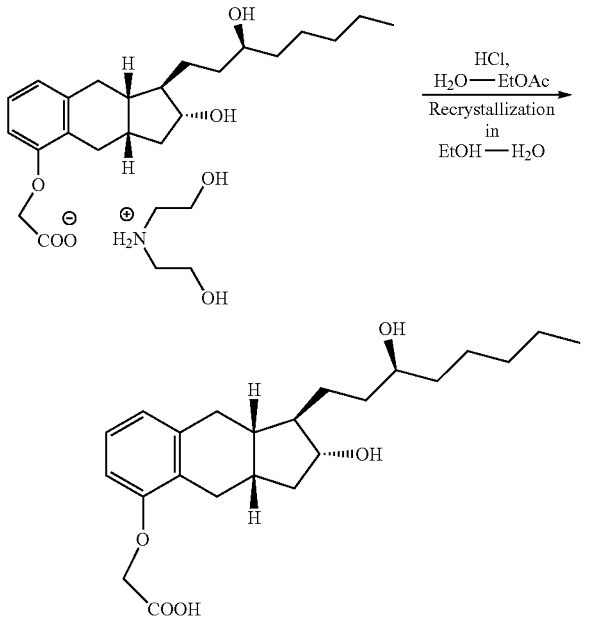

A 250-mL, round-bottom flask equipped with magnetic stirrer was charged with treprostinil diethanolamine salt (4 g) and water (40 mL). The mixture was stirred to obtain a clear solution. To the clear solution, ethyl acetate (100 mL) was added. While stirring, 3M HCl (3.2 mL) was added slowly until pH ~1 was attained. The mixture was stirred for 10 minutes and organic layer was separated. The aqueous layer was extracted with ethyl acetate (2×100 mL). The combined organic layers was washed with water (2×100 mL), brine (1×50 mL) and dried over anhydrous $Na_2SO_4$. The ethyl acetate solution of treprostinil was filtered and the filtrate was concentrated under vacuum at 50° C. to give off-white solid. The crude treprostinil was recrystallized from 50% ethanol in water (70 mL). The pure treprostinil was collected in a Buchner funnel by filtration and cake was washed with cold 20% ethanolic solution in water. The cake of treprostinil was air-dried overnight and further dried in a vacuum oven at 50° C. under high vacuum to afford 2.9 g of treprostinil (Yield 91.4%, purity (HPLC, AUC, 99.8%).

Analytical data on Treprostinil from Treprostinil Diethanolamine Salt (1:1) to Treprostinil

| Batch No. | Yield | Purity (HPLC) |
|---|---|---|
| 1 | 91.0% | 99.8% (AUC) |
| 2 | 92.0% | 99.9% (AUC) |
| 3 | 93.1% | 99.7% (AUC) |
| 4 | 93.3% | 99.7% (AUC) |
| 5 | 99.0% | 99.8% (AUC) |
| 6 | 94.6% | 99.8% (AUC) |

Example 6. Comparison of the Former Process and a Working Example of the Process According to the Present Invention

| Step No. | Steps | Former Process (Batch size: 500 g) | Working example of the Process according to the present invention (Batch size: 5 kg) |
|---|---|---|---|
| | | Nitrile | |
| 1 | Triol weight | 500 g | 5,000 g |
| 2 | Acetone | 20 L (1:40 wt/wt) | 75 L (1:15 wt/wt) |
| 3 | Potassium carbonate | 1,300 g (6.4 eq) | 5,200 g (2.5 eq) |
| 4 | Chloroacetonitrile | 470 g (4.2 eq) | 2,270 g (2 eq) |
| 5 | Tetrabutylammonium bromide | 42 g (0.08 eq) | 145 g (0.03 eq) |
| 6 | Reactor size | 72-Liter | 50- gallon |
| 7 | Reflux time | 8 hours | No heating, Room temperature (r.t.) 45 h |
| 8 | Hexanes addition before filtration | Yes (10 L) | No |
| 9 | Filter | Celite | Celite |
| 10 | Washing | Ethyl acetate (10 L) | Acetone (50 L) |
| 11 | Evaporation | Yes | Yes |
| 12 | Purification | Silica gel column Dichloromethane: 0.5 L Ethyl acetate: 45 L Hexane: 60 L | No column |
| 13 | Evaporation after column | Yes | No |
| 14 | Yield of nitrite | 109-112% | Not checked |
| | | Treprostinil (intermediate) | |
| 15 | Methanol | 7.6 L (50-L reactor) | 50 L (50-gal reactor) |
| 16 | Potassium hydroxide | 650 g (8 eq) | 3,375 g (4 eq) |
| 17 | Water | 2.2 L | 17 L |
| 18 | % of KOH | 30% | 20% |
| 19 | Reflux time | 3-3.5 h | 4-5 h |
| 20 | Acid used | 2.6 L (3M) | 12 L (3M) |
| 21 | Removal of impurities | 3 × 3 L Ethyl acetate | 2 × 20 L Ethyl acetate |
| 22 | Acidification | 0.7 L | 6.5 L |
| 23 | Ethyl acetate extraction | 5 × 17 L = 35 L | 90 + 45 + 45 = 180 L |
| 24 | Water washing | 2 × 8 L | 3 × 40 L |
| 25 | Sodium bicarbonate washing | Not done | 120 g in 30 L water + 15 L brine |
| 26 | Brine washing | Not done | 1 × 40 L |
| 27 | Sodium sulfate | 1 kg | Not done |
| 28 | Sodium sulfate filtration | Before charcoal, 6 L ethyl acetate | N/A |
| 29 | Charcoal | 170 g, reflux for 1.5 h, filter over Celite, 11 L ethyl acetate | Pass hot solution (75° C.) through charcoal cartridge and clean filter, 70 L ethyl acetate |
| 30 | Evaporation | Yes, to get solid intermediate treprostinil | Yes, adjust to 150 L solution |
| | | Treprostinil Diethanolamine Salt | |
| 31 | Salt formation | Not done | 1,744 g diethanolamine, 20 L ethanol at 60-75° C. |
| 32 | Cooling | N/A | To 20° C. over weekend; add 40 L ethyl acetate; cooled to 10° C. |
| 33 | Filtration | N/A | Wash with 70 L ethyl acetate |
| 34 | Drying | N/A | Air-dried to constant wt., 2 days |
| | | Treprostinil (from 1.5 kg Treprostinil diethanolamine salt) | |
| 35 | Hydrolysis | N/A | 15 L water + 25 L ethyl acetate + HCl |
| 36 | Extraction | N/A | 2 × 10 L ethyl acetate |
| 37 | Water wash | N/A | 3 × 10 L |
| 38 | Brine wash | N/A | 1 × 10 L |
| 39 | Sodium sulfate | N/A | 1 kg, stir |
| 40 | Filter | N/A | Wash with 6 L ethyl acetate |
| 41 | Evaporation | N/A | To get solid, intermediate Treprostinil |
| 42 | Crude drying on tray | 1 or 3 days | Same |
| 43 | Ethanol & water for cryst. | 5.1 L + 5.1 L | 10.2 L + 10.2 L (same %) |
| 44 | Crystallization in | 20-L rotavap flask | 50-L jacketed reactor |
| 45 | Temperature of crystallization | 2 h r.t., fridge −0° C. 24 h | 50° C. to 0° C. ramp, 0° C. overnight |

-continued

| Step No. | Steps | Former Process (Batch size: 500 g) | Working example of the Process according to the present invention (Batch size: 5 kg) |
|---|---|---|---|
| 46 | Filtration | Buchner funnel | Aurora filter |
| 47 | Washing | 20% (10 L) cooled ethanol-water | 20% (20 L) cooled ethanol-water |
| 48 | Drying before oven | Buchner funnel (20 h) Tray (no) | Aurora filter (2.5 h) Tray (4 days) |
| 49 | Oven drying | 15 hours, 55° C. | 6-15 hours, 55° C. |
| 50 | Vacuum | <−0.095 mPA | <5 Torr |
| 51 | UT-15 yield weight | ~535 g | ~1,100 g |
| 52 | % yield from triol) | ~91% | ~89% |
| 53 | Purity | ~99.0% | 99.9% |

The quality of treprostinil produced according to this invention is excellent. The purification of benzindene nitrile by column chromatography is eliminated. The impurities carried over from intermediate steps (i.e. alkylation of triol and hydrolysis of benzindene nitrile) are removed during the carbon treatment and the salt formation step. Additional advantages of this process are: (a) crude treprostinil salts can be stored as raw material at ambient temperature and can be converted to treprostinil by simple acidification with diluted hydrochloric acid, and (b) the treprostinil salts can be synthesized from the solution of treprostinil without isolation. This process provides better quality of final product as well as saves significant amount of solvents and manpower in purification of intermediates.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety.

What is claimed is:

1. A pharmaceutical composition comprising treprostinil or a pharmaceutically acceptable salt thereof, said composition prepared by a process comprising providing a starting batch of treprostinil having one or more impurities resulting from prior alkylation and hydrolysis steps, forming a salt of treprostinil by combining the starting batch and a base, and preparing a pharmaceutical composition comprising treprostinil or a pharmaceutically acceptable salt thereof from the isolated treprostinil salt, whereby a level of one or more impurities found in the starting batch of treprostinil is lower in the pharmaceutical composition, wherein said alkylation is alkylation of benzindene triol.

2. The pharmaceutical composition of claim 1, wherein the salt is isolated in crystalline form.

3. The pharmaceutical composition of claim 1, wherein the base is selected from the group consisting of sodium, ammonia, potassium, calcium, ethanolamine, diethanolamine, N-methylglucamine, and choline.

4. The pharmaceutical composition of claim 3, wherein the base is diethanolamine.

5. The pharmaceutical composition of claim 1, wherein the base is combined with treprostinil that has not been previously isolated.

6. The pharmaceutical composition of claim 1, wherein the isolated salt is stored at ambient temperature.

7. The pharmaceutical composition of claim 1, which is a pharmaceutical solution.

8. A process of preparing a pharmaceutical product comprising treprostinil or a pharmaceutically acceptable salt thereof, comprising alkylating a triol intermediate of the formula:

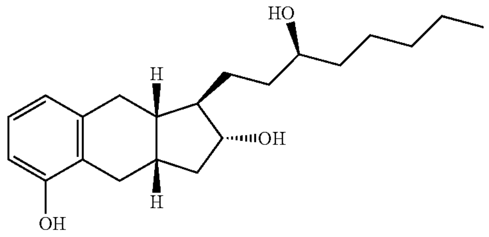 [SMILES: CCCCC[C@H](O)CC[C@@H]1[C@H]2Cc3cccc(O)c3C[C@H]2C[C@H]1O]

hydrolyzing the resulting compound to form treprostinil, forming a salt of treprostinil stable at ambient temperature, storing the treprostinil salt at ambient temperature, and preparing a pharmaceutical product from the treprostinil salt after storage, wherein the pharmaceutical product comprises treprostinil or a pharmaceutically acceptable salt thereof.

9. A pharmaceutical product prepared by the process of claim 8.

10. The process as claimed in claim 8, wherein forming the salt of treprostinil stable at ambient temperature is performed by adding diethanolamine to treprostinil.

* * * * *